United States Patent
Kaukler et al.

(10) Patent No.: US 8,490,470 B1
(45) Date of Patent: Jul. 23, 2013

(54) PARALLEL PLATE SYSTEM FOR COLLECTING DATA USED TO DETERMINE VISCOSITY

(75) Inventors: William Kaukler, Huntsville, AL (US); Edwin C. Ethridge, Huntsville, AL (US)

(73) Assignee: The United States of America as Represented by the Administrator of the National Aeronautics and Space Administration, Washington, DC (US)

(*) Notice: Subject to any disclaimer, the term of this patent is extended or adjusted under 35 U.S.C. 154(b) by 796 days.

(21) Appl. No.: 12/569,555

(22) Filed: Sep. 29, 2009

(51) Int. Cl.
*G01N 11/00* (2006.01)

(52) U.S. Cl.
USPC ....... 73/54.01; 73/54.23; 73/54.37; 73/54.38; 73/54.39

(58) Field of Classification Search
USPC ............. 73/23, 37, 38, 39, 54.01–54.43
See application file for complete search history.

(56) References Cited

U.S. PATENT DOCUMENTS

| | | | | |
|---|---|---|---|---|
| 2,233,770 A * | 3/1941 | Campbell | | 239/485 |
| 3,719,075 A * | 3/1973 | Mandrona et al. | | 73/54.27 |
| 4,674,322 A * | 6/1987 | Stangeland | | 73/32 A |
| 5,279,149 A | 1/1994 | Williams et al. | | |
| 5,319,958 A * | 6/1994 | Date et al. | | 73/53.01 |
| 5,705,738 A * | 1/1998 | Kurihara | | 73/54.39 |
| 6,023,962 A | 2/2000 | Wang et al. | | |
| 6,668,622 B2 | 12/2003 | Hajduk et al. | | |
| 6,951,083 B2 * | 10/2005 | Kim | | 52/167.9 |
| 7,290,441 B2 | 11/2007 | Baek | | |
| 2004/0093932 A1 * | 5/2004 | Hajduk et al. | | 73/54.39 |
| 2008/0134765 A1 | 6/2008 | Baek | | |

FOREIGN PATENT DOCUMENTS

GB 2233770 A * 1/1991

* cited by examiner

*Primary Examiner* — Hezron E Williams
*Assistant Examiner* — Hoang Nguyen
(74) *Attorney, Agent, or Firm* — Peter J. Van Bergen; James J. McGroary

(57) ABSTRACT

A parallel-plate system collects data used to determine viscosity. A first plate is coupled to a translator so that the first plate can be moved along a first direction. A second plate has a pendulum device coupled thereto such that the second plate is suspended above and parallel to the first plate. The pendulum device constrains movement of the second plate to a second direction that is aligned with the first direction and is substantially parallel thereto. A force measuring device is coupled to the second plate for measuring force along the second direction caused by movement of the second plate.

20 Claims, 2 Drawing Sheets

PARALLEL PLATE SYSTEM FOR COLLECTING DATA USED TO DETERMINE VISCOSITY

Figure 1:
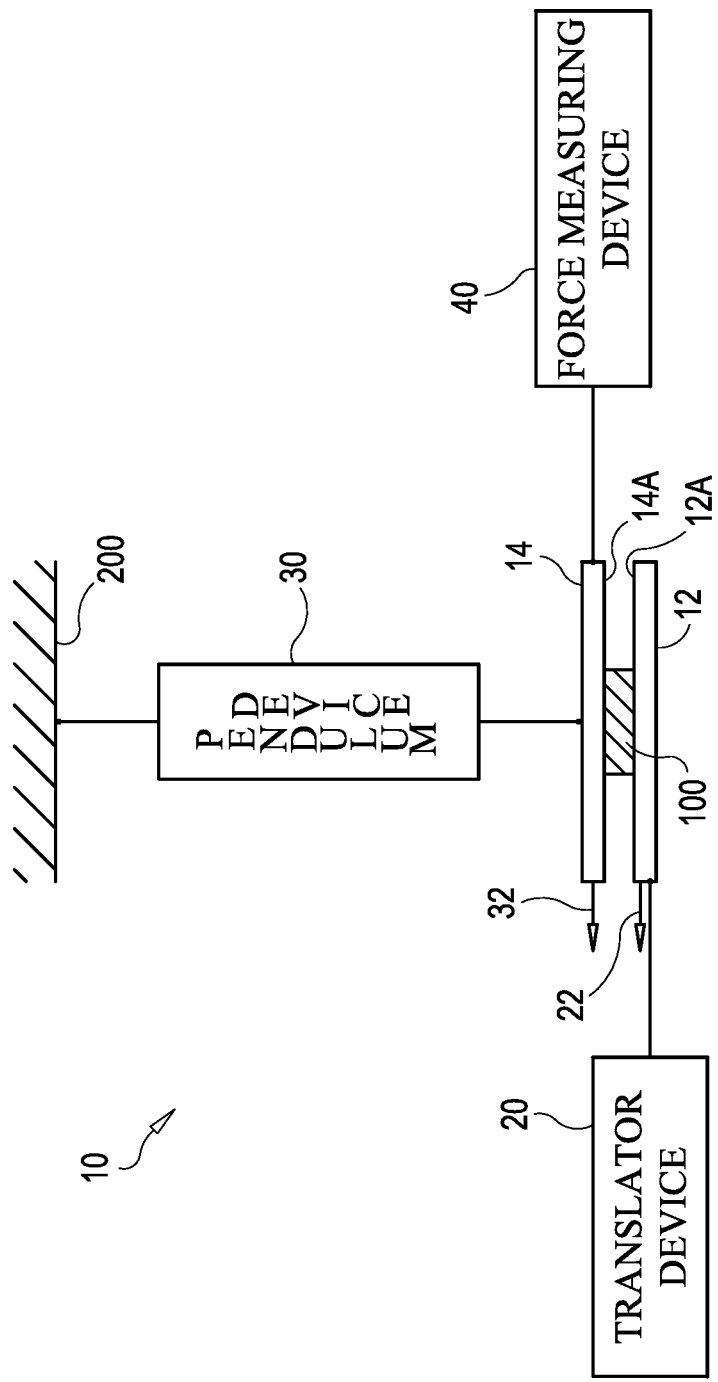

The invention described herein was made in the performance of work under a NASA contract and by an employee of the United States Government and is subject to the provisions of Public Law 96-517 (35 U.S.C §202) and may be manufactured and used by or for the Government for governmental purposes without the payment of any royalties thereon or therefore. In accordance with 35 U.S.C §202, the contractor elected not to retain title.

BACKGROUND OF THE INVENTION

1. Field of the Invention

This invention relates to measurement of viscosity. More specifically, the invention is a parallel plate system that collects data that can be used to determine viscosity.

2. Description of the Related Art

The classic principle of viscosity envisions that a liquid or viscous material under test is uniformly sheared between two parallel plates with the resulting resistance to the shear being measured in the direction of shearing. Using this ideal set-up, the amount and rate of shear will be uniform over the full volume of the material under test. However, this classic and ideal arrangement is not practiced by most commercially-available instruments. Rather, commercial viscometers (i.e., used for low viscosity materials) and rheometers (i.e., used for higher viscosity materials) typically dispose a material under test between rotating disks or cylinders, and then measure the resistance to rotation in order to determine viscosity. However, the shear forces measured by these apparatus will vary with radius. Accordingly, the viscosity determinations made with these shear force measurements are not an absolute viscosity.

SUMMARY OF THE INVENTION

Accordingly, it is an object of the present invention to provide a system that can produce and collect classic parallel-plate shear data for use in determining viscosity.

Another object of the present invention is to provide a system that can produce and collect parallel-plate shear data in a variety of temperature environments.

Other objects and advantages of the present invention will become more obvious hereinafter in the specification and drawings.

In accordance with the present invention, a system is provided for collecting data used to determine viscosity. A first plate having a planar surface is coupled to a translator so that the first plate can be moved along a first direction aligned with the planar surface thereof. A second plate having a planar surface has a pendulum device coupled thereto such that the second plate is suspended above the first plate with the planar surface of the second plate maintained parallel to the planar surface of the first plate.

The pendulum device further constrains movement of the second plate to a second direction that is aligned with the first direction and is substantially parallel thereto when the second plate is suspended above the first plate. A force measuring device is coupled to the second plate for measuring force along the second direction caused by movement of the second plate.

BRIEF DESCRIPTION OF THE DRAWING(S)

Figure 2:
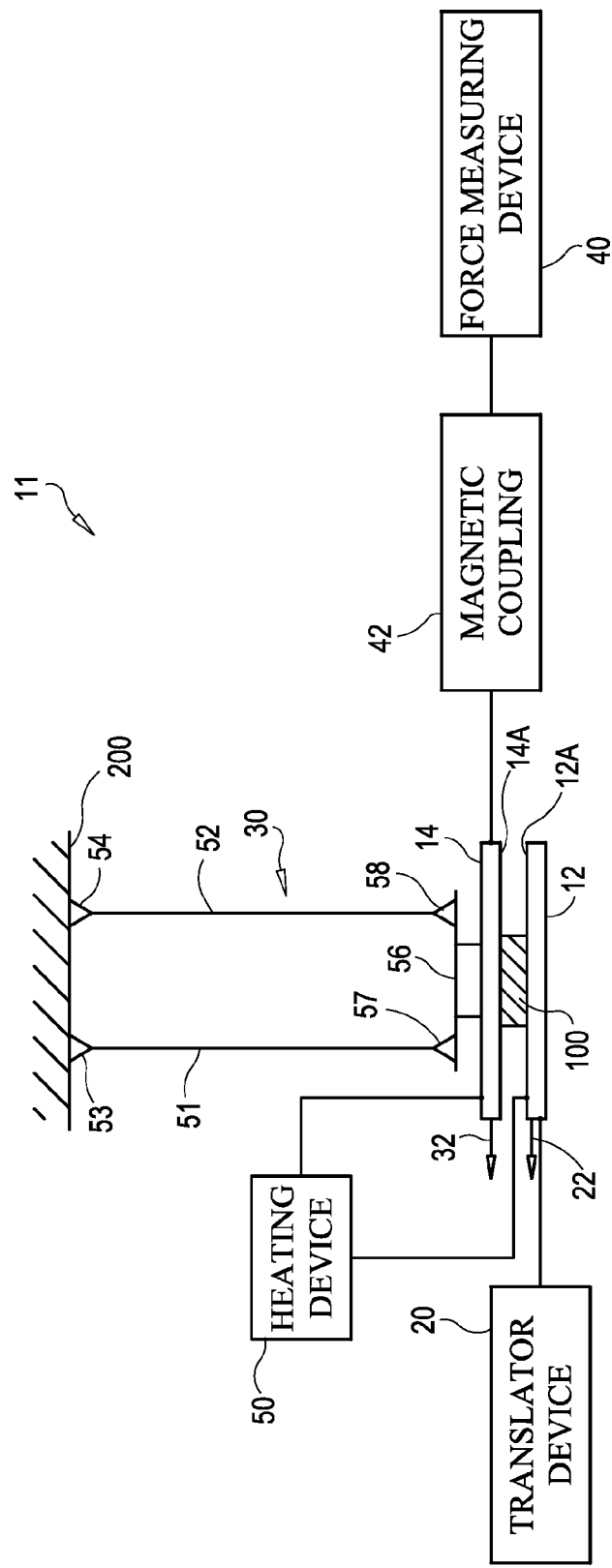

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is a schematic view of a system for collecting data used to determine a material's viscosity in accordance with an embodiment of the present invention; and FIG. 2 is a schematic view of a system for collecting data used to determine a material's viscosity at high temperatures in accordance with another embodiment of the present invention.

DESCRIPTION OF THE PREFERRED EMBODIMENT(S)

Referring now to the drawings and more particularly to FIG. 1, a system for collecting data that can be used in the determination of a material's viscosity is shown and is referenced generally by numeral 10. In general, system 10 provides a user with both shear rate and shear stress data. As is known in the art, viscosity is the ratio of shear stress to shear rate. As will be explained further herein, system 10 can be readily configured to collect data on low-viscosity materials (i.e., liquids) as well as high-viscosity materials such as glass or other non-Newtonian-behaving materials such as polymers or rubbers. Still further, system 10 can be readily configured to collect accurate shear data at a variety of temperatures to include high temperatures needed to make certain materials (e.g., glass) behave in a viscous fashion.

System 10 provides a structure that realizes the classic parallel-plate principle of viscosity where shear stress and sheer rate data are accurately measured such that an accurate viscosity determination is possible. Accordingly, system 10 includes two plates 12 and 14 that are maintained in a parallel relationship throughout relative one-dimensional movement with a "material under test" (MUT) 100 disposed therebetween. Each of plates 12 and 14 is made from rigid material that defines respective planar surfaces 12A and 14A that oppose one another in system 10. The size and shape of plates 12 and 14 are not limitations of the present invention, and the materials used for plates 12 and 14 include a variety of non-transparent materials (e.g., graphite, invar, iridium, platinum, silicon carbide, silicon nitride) or transparent materials (e.g., a quartz such as vitreous quartz, mica, sapphire, a thin plate of stabilized zirconia). If one or both of plates 12 and 14 is transparent (or at least transparent in the locale of MUT 100) so that the area of MUT 100 can be readily monitored or measured, the gap dimension between plates 12 and 14 can be readily determined and monitored based on the area of MUT 100 and the volume thereof placed between plates 12 and 14. Further, the use of vitreous quartz provides for testing of MUT's at high temperatures up to 800° C. or more owing to its very low thermal coefficient of expansion. This is important when the MUT (e.g., glass) is viscous only at high temperatures. If necessary, plates 12/14 and MUT 100 (or all of system 10) can be contained in a protective inert gas or vacuum environment.

In order to create uniform shear required to implement the principle of viscosity, plate 12 is coupled to a translator device 20 and plate 14 is coupled to a pendulum device 30. Translator device 20 applies an in-plane force to plate 12 such that it moves in a single dimension/direction that coincides with the plane of surface 12A. In the illustrated embodiment, the direction of force/motion imparted by translator device 20 is indicated by arrow 22. Typically, translator device 20 is a controllable motorized device imparting a known rate of translation to plate 12.

Pendulum device 30 is coupled on one end thereof to an overhead support 200 and on the other end thereof to plate 14. In general, pendulum device 30 suspends plate 14 over plate 12 with planar surfaces 12A and 14A (i) spaced apart from one another by a specified gap dimension, and (ii) maintained in a parallel relationship. Pendulum device 30 should further be configured to restrict movement of plate 14 to be in directional alignment with and parallel to direction as indicated by arrow 32. Pendulum device 30 should maintain the parallel relationship between plates 12 and 14 throughout the expected range of displacement of plates 12 and 14. By way of example, pendulum device 30 can be a parallel pendulum having two spaced-apart pendulum arms (not shown) aligned with directions 22 and 32. The vertical position of support 200 and/or the length of and spacing between two such pendulum arms can be adjusted to maintain the parallel relationship between plates 12 and 14 for a given test set-up.

A force measurement device/sensor 40 (e.g., a load cell or strain gage) is coupled to plate 14. Sensor 40 measures the amount of shear force translated to plate 14 (in direction 32) by MUT 100 as plate 12 is moved (in direction 22) by translator device 20. Coupling of sensor 40 to plate can be made by means of simple magnetic coupling (not shown) in order to eliminate alignment problems.

The present invention can be realized by a variety of system constructions without departing from the scope of thereof. One such system is illustrated in FIG. 2 and referenced generally by numeral 11. In system 11, each of plates 12 and 14 is a vitreous quartz plate thereby allowing system 11 to be used with MUTs that must be heated for testing purposes. Accordingly, a heating device 50 applies heat to plates 12 and 14 (as shown) or to the environment that includes plates 12/14 and MUT 100. Pendulum device 30 is realized with a parallel pendulum having spaced-apart parallel rods 51 and 52 made from vitreous quartz so that the lengths of rods 51 and 52 will not change with temperature, i.e., vitreous quartz's thermal coefficient of expansion is extremely small. Rods 51 and 52 lie in a plane that is aligned with directions 22 and 32, i.e., the plane of the paper in the illustration. The top ends of rods 51 and 52 are supported at support 200 by means of respective bearings 53 and 54 providing single degree of freedom aligned with directions 22 and 32. Similarly, the bottom ends of rods 51 and 52 are supported at a plate support 56 by means of respective bearings 57 and 58 providing a single degree of freedom aligned with directions 22 and 32. Plate support 56 is coupled to plate 14. Bearings 53, 54, 57 and 58 can be any single-degree of freedom bearings such as knife-edge bearings or jeweled bearings. The length of rods 51 and 52 and spacing therebetween are selected such that plates 12/14 remain parallel throughout the expected amount of movement of plate 14. A magnetic coupling 42 is provided to couple plate to force measuring device 40 in order to eliminate alignment errors therebetween.

In operation with MUT 100 placed between 12 and 14, heating device 50 is used (if needed) to apply the requisite amount of heat for testing MUT 100. Translator device 20 moves plate 12 in direction 22 at a known velocity. The known velocity along with the known (or measured) gap dimension between plates 12 and 14 establishes the shear rate. Gap dimension can be readily determined and monitored by, for example, non-contact laser beam triangulation sensors, fiber optic sensors, or capacitance sensors (not shown) as would be understood by one of ordinary skill in the art. Movement of plate 12 introduces a shear force in MUT 100 that, in turn, is applied to plate 14 to move same in direction 32. The area of MUT 100, it thickness, and its viscosity establish the load or viscous drag that is measured by force measuring device 40. This load divided by the area of MUT 100 yields the shear stress. Finally, viscosity is determined by taking the ratio of shear stress to shear rate.

The advantages of the present invention are numerous. The classic parallel-plate viscosity set-up has finally been realized. The pendulum mounting of the upper plate eliminates noise as only lateral shear force is measured by the force measuring sensor coupled thereto. The fixture and mass of the MUT do not interfere with the upper plate load measurement. Furthermore, only small displacements of the lower plate are required to generate a measurement. This is of particular importance when collecting data for viscous glasses. Use of vitreous quartz for various key elements of the system assures stable operation across a wide range of temperatures since vitreous quartz has a small thermal coefficient of expansion.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A system for collecting data used to determine viscosity, comprising:
   a first plate having a planar surface;
   a translator coupled to said first plate for moving said first plate along a first direction aligned with said planar surface thereof;
   a second plate having a planar surface;
   a pendulum device coupled to said second plate for suspending said second plate above said first plate wherein said planar surface of said second plate is parallel to said planar surface of said first plate, said pendulum device further constraining movement of said second plate to a second direction that is aligned with said first direction and is substantially parallel thereto when said second plate is suspended above said first plate; and
   a force measuring device coupled to said second plate for measuring force along said second direction caused by movement of said second plate.

2. The system as in claim 1, wherein said first plate and said second plate comprise an identical material.

3. The system as in claim 1, wherein said first plate and said second plate comprise different materials.

4. The system as in claim 1, wherein at least one of said first plate and said second plate is transparent.

5. The system as in claim 1, wherein said first plate and said second plate are selected from the group consisting of graphite, invar, iridium, mica, platinum, sapphire, silicon carbide, silicon nitride, stabilized zirconia, and vitreous quartz.

6. The system as in claim 1, wherein a region is defined between said first plate and said second plate when said second plate is suspended over said first plate, said system further comprising means for heating said region.

7. The system as in claim 1, wherein said pendulum device comprises a parallel pendulum.

8. The system as in claim 7, wherein said parallel pendulum includes parallel quartz rods.

9. The system as in claim 1, further comprising a magnetic coupling for coupling said force measuring device to said second plate.

10. A system for collecting data used to determine viscosity, comprising:
    a first plate having a planar surface;

a translator coupled to said first plate for moving said first plate along a first direction aligned with said planar surface thereof;

a second plate having a planar surface;

a parallel-support pendulum coupled to said second plate for suspending said second plate above said first plate wherein said planar surface of said second plate is parallel to said planar surface of said first plate, said pendulum including two spaced-apart rigid and parallel support rods with spacing between said rods and length of said rods selected to constrain movement of said second plate to a second direction that is aligned with said first direction and is substantially parallel thereto when said second plate is suspended above said first plate; and a force measuring device coupled to said second plate for measuring force along said second direction caused by movement of said second plate.

11. The system as in claim 10, wherein said rods comprise quartz rods.

12. The system as in claim 10, wherein said first plate and said second plate comprise an identical material.

13. The system as in claim 10, wherein said first plate and said second plate comprise different materials.

14. The system as in claim 10, wherein at least one of said first plate and said second plate is transparent.

15. The system as in claim 10, wherein said first plate and said second plate are selected from the group consisting of graphite, invar, iridium, mica, platinum, sapphire, silicon carbide, silicon nitride, stabilized zirconia, and vitreous quartz.

16. The system as in claim 10, wherein a region is defined between said first plate and said second plate when said second plate is suspended over said first plate, said system further comprising means for heating said region.

17. The system as in claim 10, further comprising a magnetic coupling for coupling said force measuring device to said second plate.

18. A system for collecting data used to determine viscosity, comprising:

a first quartz plate having a planar surface;

a translator coupled to said first quartz plate for moving said first quartz plate along a first direction aligned with said planar surface thereof;

a second quartz plate having a planar surface;

a parallel-support pendulum coupled to said second quartz plate for suspending said second quartz plate above said first quartz plate wherein said planar surface of said second quartz plate is parallel to said planar surface of said first quartz plate, said pendulum including two spaced-apart rigid and parallel quartz rods with spacing between said quartz rods and length of said quartz rods selected to constrain movement of said second quartz plate to a second direction that is aligned with said first direction and is substantially parallel thereto when said second quartz plate is suspended above said first quartz plate; and a force measuring device coupled to said second quartz plate for measuring force along said second direction caused by movement of said second quartz plate.

19. The system as in claim 18, wherein a region is defined between said first quartz plate and said second quartz plate when said second quartz plate is suspended over said first quartz plate, said system further comprising means for heating said region.

20. The system as in claim 18, further comprising a magnetic coupling for coupling said force measuring device to said second quartz plate.

* * * * *